US00PP19213P2

(12) United States Plant Patent
Chen

(10) Patent No.: US PP19,213 P2
(45) Date of Patent: Sep. 9, 2008

(54) ***CORDYLINE* PLANT NAMED 'SPRILECPINK'**

(50) Latin Name: *Cordyliine banksii*
Varietal Denomination: Sprilecpink

(75) Inventor: Jianping Chen, Zhejiang (CH)

(73) Assignee: Sprint Horticulture Pty. Ltd., Wamberal, New South Wales (AU)

( * ) Notice: Subject to any disclaimer, the term of this patent is extended or adjusted under 35 U.S.C. 154(b) by 0 days.

(21) Appl. No.: 11/728,154

(22) Filed: Mar. 23, 2007

(51) Int. Cl.
*A01H 5/00* (2006.01)

(52) U.S. Cl. ..... Plt./383
(58) Field of Classification Search ..... Plt./383
See application file for complete search history.

*Primary Examiner*—Annette H Para
(74) *Attorney, Agent, or Firm*—C. A. Whealy

(57) ABSTRACT

A new and distinct cultivar of *Cordyline* plant named 'Sprilecpink', characterized by its upright and outwardly arching growth habit; multiple stems per plant; long arching linear leaves with red purple, greyed purple and brown-colored longitudinal stripes; and good keeping quality and garden performance.

2 Drawing Sheets

Botanical designation: *Cordyline banksii.*
Cultivar denomination: 'SPRILECPINK'.

BACKGROUND OF THE INVENTION

The present invention relates to a new and distinct cultivar of *Cordyline* plant, botanically known as *Cordyline banksii,* and hereinafter referred to by the name 'Sprilecpink'.

The new *Cordyline* is a naturally-occurring whole plant mutation of the *Cordyline banksii* cultivar CAZ50, not patented. The new *Cordyline* was discovered and selected by the Inventor within a population of plants of the parent selection in a controlled environment in Zhejiang, China in August, 2003.

Asexual reproduction of the new *Cordyline* by micropropagated cuttings in Zhejiang, China since August, 2003, has shown that the unique features of this new *Cordyline* are stable and reproduced true to type in successive generations.

SUMMARY OF THE INVENTION

The cultivar Sprilecpink has not been observed under all possible environmental conditions. The phenotype may vary somewhat with variations in environment such as temperature and light intensity, without, however, any variance in genotype.

The following traits have been repeatedly observed and are determined to be the unique characteristics of 'Sprilecpink'. These characteristics in combination distinguish 'Sprilecpink' as a new and distinct cultivar of *Cordyline:*

1. Upright and outwardly arching growth habit.
2. Multiple stems per plant.
3. Long arching linear leaves with red purple, greyed purple and brown colored longitudinal stripes.
4. Good keeping quality and garden performance.

Plants of the new *Cordyline* differ from plants of the parent, the cultivar CAZ50, primarily in foliage color as plants of the cultivar CAZ50 have purple-colored leaves. In addition, plants of the new *Cordyline* are more outwardly arching than and not as upright as plants of the cultivar CAZ50.

Plants of the new *Cordyline* can be compared to plants of the *Cordyline banksii* cultivar Pink Sensation, not patented. Plants of the new *Cordyline* differ primarily from plants of the cultivar Pink Sensation in plant form as plants of the cultivar Pink Sensation do not have multiple stems. In addition, plants of the new *Cordyline* are shorter and have shorter stems than plants of the cultivar Pink Sensation.

Plants of the new *Cordyline* can be compared to plants of the *Cordyline banksii* cultivar Purple Sensation, not patented. Plants of the new *Cordyline* differ from plants of the cultivar Purple Sensation in the following characteristics:

1. Plants of the new *Cordyline* were shorter than and not as broad as plants of the cultivar Purple Sensation.
2. Plants of the new *Cordyline* have narrower leaves than plants of the cultivar Purple Sensation.
3. Plants of the new *Cordyline* and the cultivar Purple Sensation differ in leaf coloration as plants of the cultivar Purple Sensation have brown-colored leaves with a purple-colored midrib.

BRIEF DESCRIPTION OF THE PHOTOGRAPHS

The accompanying photographs illustrates the overall appearance of the new *Cordyline.* This photographs show the colors as true as it is reasonably possible to obtain in colored reproductions of this type. Colors in the photographs may differ slightly from the color values cited in the detailed botanical description which accurately describe the colors of the new *Cordyline.*

The photograph on the first sheet comprises a side perspective view of a typical plant of 'Sprilecpink' grown in a container.

The photograph on the second sheet is a top perspective view of a typical close-up view of a typical plant of 'Sprilecpink' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Wamberal, New South Wales, Australia during the spring and summer in an outdoor nursery and under conditions and practices which approximate those generally used in commercial *Cordyline* production. During the production of the plants, day temperatures ranged from 18° C. to 32° C. night temperatures ranged from 7° C. to 18° C. and light levels were about 100,000 lux. Plants were about 18 months old when the photographs and the botanical description were taken.

Botanical classification: *Cordyline banksii* cultivar Sprilecpink.

Parentage: Naturally-occurring whole plant mutation of the *Cordyline banksii* cultivar CAZ50, not patented.

Propagation:

*Type.*—By micropropagated cuttings.

*Time to initiate roots, summer.*—About two weeks at 25° C. to 35° C.

*Time to initiate roots, winter.*—About three weeks at 18° C.

*Time to produce a rooted young plant, summer.*—About one to two months at 25° C.

*Time to produce a rooted young plant, winter.*—About two months at 18° C.

*Root description.*—Medium thickness, fleshy; white in color.

*Rooting habit.*—Freely branching; dense.

Plant description:

*Plant form/growth habit.*—Upright and outwardly arching plant habit; broadly inverted triangle with arching leaves. Multiple stems per plant. Vigorous growth habit.

*Plant height.*—About 120 cm.

*Plant diameter or spread.*—About 80 cm.

Stem description:

*Diameter, at base.*—About 4 cm.

*Color.*—Close to 63D; occasionally 147C to 147D.

*Texture.*—Smooth, glabrous.

Foliage description:

*Orientation.*—Initially erect to outwardly arching.

*Arrangement.*—Whorled; sessile.

*Shape.*—Linear.

*Apex.*—Acute.

*Margin.*—Entire.

*Texture, upper and lower surfaces.*—Leathery; smooth, glabrous.

*Luster, upper surface.*—Glossy.

*Luster, lower surface.*—Dull.

*Venation pattern.*—Parallel.

*Length.*—About 45 cm to 76 cm.

*Width.*—About 8 mm to 2.2 cm.

*Color.*—Developing leaves, upper and lower surfaces: Alternating longitudinal stripes of 200A and 197A to 197B; towards the base, 145C. Fully expanded leaves, upper and lower surfaces: Alternating longitudinal stripes of 59D, 186A and 200A; outer stripes along the margin, 58A. Venation, upper and lower surfaces: Similar to lamina.

Flower description: Plants of the new *Cordyline* do not typically develop flowers.

Disease/pest resistance: Plants of the new *Cordyline* have not been shown to be resistant to pathogens and pests common to *Cordyline*.

Keeping quality: Plants of the new *Cordyline* are durable and will maintain good leaf substance indefinitely under interior conditions.

Garden performance: Plants of the new *Cordyline* have been observed to have good garden performance and tolerate wind, rain and temperatures ranging from about 5° C. to about 45° C.

It is claimed:

1. A new and distinct *Cordyline* plant named 'Sprilecpink' as illustrated and described.

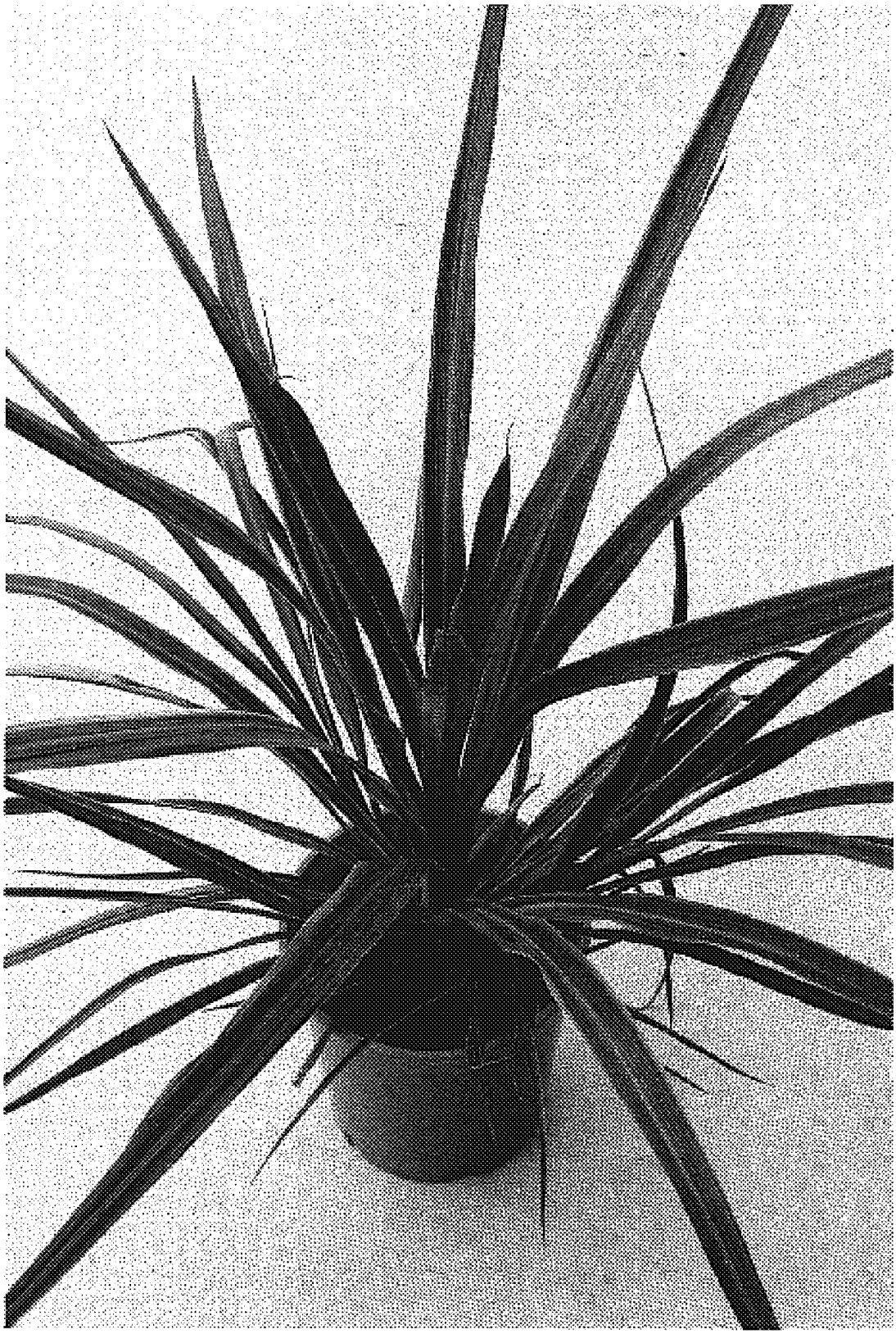

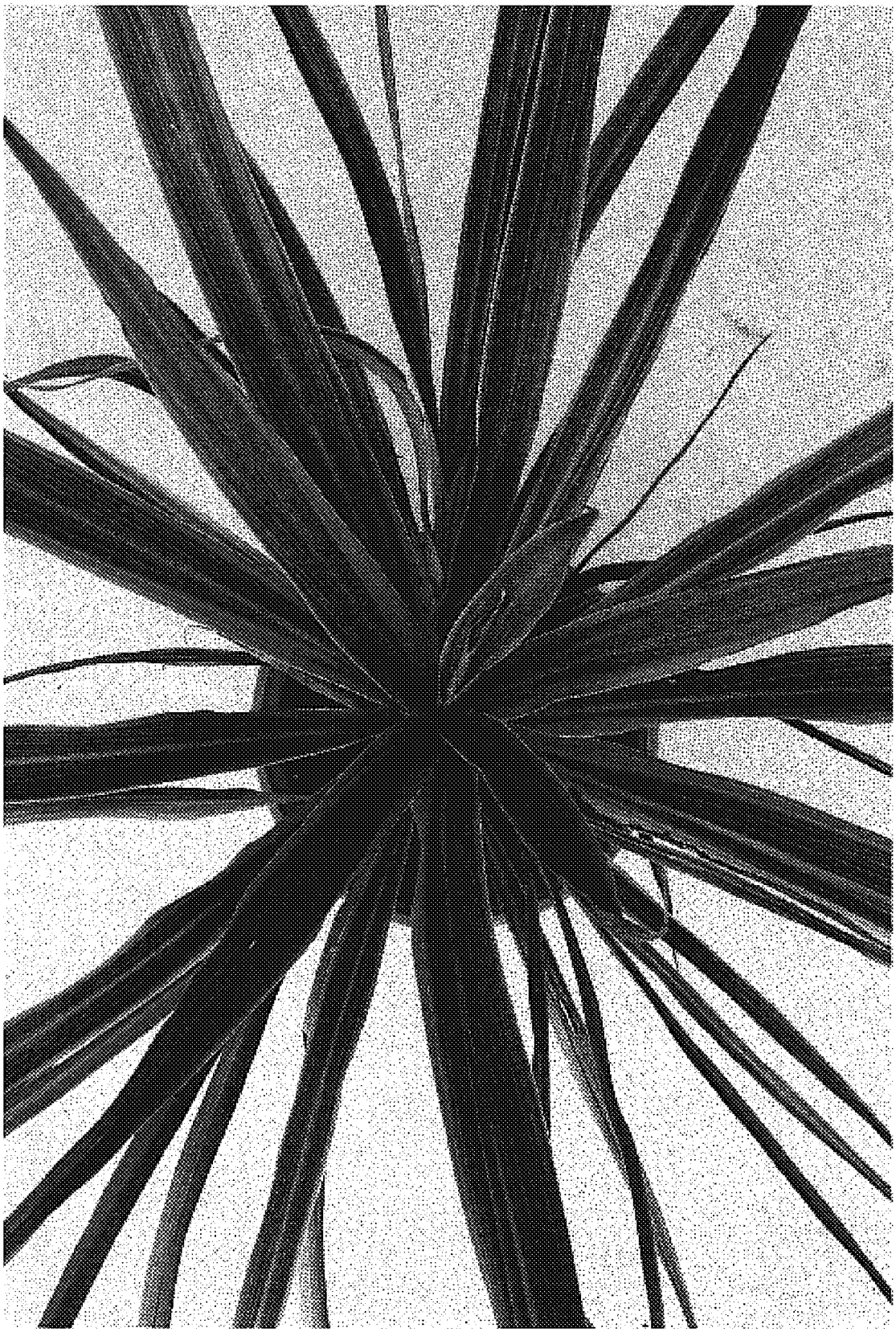

* * * * *